(12) United States Patent
Gama et al.

(10) Patent No.: US 8,623,610 B2
(45) Date of Patent: Jan. 7, 2014

(54) CHONDROITIN SULFATE BINDING PROTEINS AND MODULATORS THEREOF

(75) Inventors: Cristal I. Gama, Los Angeles, CA (US); Sarah E. Tully, Olmstead, OH (US); Linda C. Hsieh-Wilson, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 712 days.

(21) Appl. No.: 11/751,880

(22) Filed: May 22, 2007

(65) Prior Publication Data

US 2007/0275412 A1    Nov. 29, 2007

Related U.S. Application Data

(60) Provisional application No. 60/802,414, filed on May 22, 2006.

(51) Int. Cl.
  *G01N 31/00* (2006.01)
  *G01N 33/53* (2006.01)

(52) U.S. Cl.
  USPC ........... 435/7.21; 435/7.1; 436/501; 436/506; 436/518; 422/430; 530/300; 530/350; 424/9.1

(58) Field of Classification Search
  None
  See application file for complete search history.

(56) References Cited

U.S. PATENT DOCUMENTS

2006/0025379 A1    2/2006  Hsieh-Wilson et al.

OTHER PUBLICATIONS

Gama et al. (Nature Chemical Biology, vol. 2, No. 9, Sep. 2006, pp. 467-473).*
Maggio (Immunoenzyme technique I, CRC press 1980, pp. 186-187).*
Fukui et al. Oligosacchardie microarrays for high-throughput detection and specificity assignments of carbohydrate-protein interactions. Nature Biotechnology. vol. 20, No. 10. Oct. 2002, pp. 1011-1017.*
Bradbury et al., "Chondroitinase ABC promotes functional recovery after spinal cord injury," Nature col. 416, 636-640. Apr. 11, 2002.
Fournier et al., "Indentification of a receptor mediating Nogo-66 inhibition of axonal regeneration," Nature 409, 341-346 (2001).
Gama et al., "Sulfation patterns of glycosaminoglycans encode molecular recognition and activity," Nature Chemical Biology 2(9):467-473 (2006).
Habeeb, "Determination of Free Amino Groups in Proteins by Trinitrobenzenesulfonic Acid," Anal. Biochem. 14, 328-336 (1966).
Holt et al., "Sugar Codes for Axons?," Neuron 46, 169-172 (2005).
Kitagawa et al., "Developmental Regulation of the Sulfation Profile of Chodroitin Sulfate Chains in the Chicken Embryo Brain*," J. Biol Chem. 272, 31377-31381 (1997).
Marsh et al., "Signal Transduction Events Mediated by the BDNF Receptor gp145trkB in Primary Hippocampal Pyramidal Cell Culture," Journal of Neuroscience, vol. 13, 4281-4292 (1993).
Moon et al., "Regeneration of CNS axons back to their target following treatment of adult rat brain with chodroitinase ABC," Nature Neuroscience vol. 4 No. 5, May (2001).
Nandini et al., "Structural and Functional Characterization of Oversulfated Chondroitin Sulfate/Dermatan Sulfate Hybrid Chains from the Notochord of Hagfish," J. Biol. Chem. 279, 50799-50809 (2004).
Plaas et al., "Glycosaminoglycan Sulfation in Human Osteoarthritis," J. Biol. Chem. 273, 12642-12649 (1998).
Shi et al., "Luteolin sensitizes tumor necrosis factor-a-induced apoptosis in human tumor cells," Oncogene, 23 7712-7721 (2004).
Shipp & Hsieh-Wilson, "Profiling the Sulfation Specificities of Glycosaminoglycan Interactions with Growth Factors and Chemotactic Proteins Using Microarrays," Chemistry & Biology 14:195-208 (2007).
Shirayev et al., "Synthesis of Novel Adamantylalkoxyurea Derivatives from 2-(1-Adamantylimino)-1,3-oxathiolane," Journal of Synthetic Organic Chemistry, No. 1, 38-40 (1997).
Taylor et al., "A Colorimetric Method for the Quantitation of Uronic Acids and a Specific Assay for Glacturonic Acid," Anal. Biochem. 201, 190-196 (1992).
Tully et al., "A Chondroitin Sulfate Small Molecule that Stimulates Neuronal Growth," J. Am Chem. Soc. 126, 7736-7736 (2004).
Tully et al., "Discovery of a TNF-∞ Antagonist Using Chondroitin Sulfate Microarrays," J. Am. Clime. Soc. 128:7740-7741 (2006).
Yeung et al., "An Essential Role for the Interferon-Inducible, Double-Stranded RNA-Activated Protein Kinase PKR in the Tumor Necrosis Factor-Induced Apoptis in U937 Cells," Proc. Natl. Sci. USA 93, 12451-12455, (1996).

* cited by examiner

Primary Examiner — Lisa Cook
(74) Attorney, Agent, or Firm — Wilson Sonsini Goodrich & Rosati

(57) ABSTRACT

Chondroitin sulfate polysaccharides with defined sulfation patterns can be synthesized. These chondroitin polysaccharides can be used to identify chondroitin sulfate binding proteins. Further, compounds that modulate the activity of chondroitin sulfate binding proteins can be identified. For example, TNF-α was found to bind specifically to CS-E and CS-E can be used to modulate the interaction of TNF-α with the TNF receptor.

16 Claims, 6 Drawing Sheets

CS-E (1)

1. SO$_3$•TMA (50 equiv.), DMF, 50 °C, 84%
2. HF•pyr, 0 °C, 91%
3. 1 M LiOH, 30% H$_2$O$_2$, 0 °C
4. NaOH, MeOH, H$_2$O
70% (2 steps)

CS-C (2)

1. SO$_3$•TMA (5 equiv.), DMF, 50 °C, 61%
2. HF•pyr, 0 °C, 89%
3. 1 M LiOH, 30% H$_2$O$_2$, 0 °C
4. NaOH, MeOH, H$_2$O
quant. (2 steps)

FIG. 1D

CHONDROITIN SULFATE BINDING PROTEINS AND MODULATORS THEREOF

CROSS-REFERENCE TO RELATED APPLICATIONS

This application claims priority to U.S. Provisional Application No. 60/802,414, filed May 22, 2006. The priority application is incorporated herein by reference in its entirety.

STATEMENT REGARDING FEDERALLY SPONSORED R&D

The U.S. Government has certain rights in this invention pursuant to Grant No. NS045061 awarded by the National Institutes of Health.

BACKGROUND OF THE INVENTION

1. Field of the Invention

The invention relates generally to chondroitin sulfate and chondroitin sulfate binding proteins. Methods for identifying chondroitin sulfate binding proteins and methods for identifying compounds that modulate the activity of chondroitin sulfate binding proteins are provided, as are methods of using such proteins and compounds.

2. Description of the Related Art

Glycosaminoglycans have an inherent capacity to encode functional information that rivals DNA, RNA and proteins. Specifically, these polysaccharides display diverse patterns of sulfation that are tightly regulated in vivo. Kitagawa, H. et al., *J. Biol. Chem.* 272, 31377-31381 (1997). Plaas, A. H. K. et al., *J. Biol. Chem.* 273, 12642-12649 (1998). Chondroitin sulfate (CS) glycosaminoglycans play important roles in biological processes such as neural development, viral invasion, cancer metastasis and spinal cord injury. The three major sulfation motifs found in vivo CS-A, CS-C and CS-E, differ only subtly in their sulfation pattern and are identical in terms of stereochemistry and sugar composition. The diverse sulfation patterns of CS polysaccharides have been postulated to function as molecular recognition motifs for growth factors, chemokines and other proteins. However, until now, no method existed to rapidly identify CS-binding proteins or specific sulfation motifs involved in protein recognition.

SUMMARY OF THE INVENTION

Methods for identifying a chondroitin sulfate binding protein are disclosed in accordance with some embodiments of the present invention. In some embodiments, such a method comprises the steps of: providing one or more chondroitin sulfates; contacting one or more test proteins to the chondroitin sulfate; and identifying test proteins that bind to the chondroitin sulfate. The chondroitin sulfate may be bound to a solid support, such as a cell, a glass slide a bead or a microtiter plate. In other embodiments the chondroitin sulfate may be in solution.

Test proteins that are able to bind chrondroitin sulfate can be identified, for example by an immunoassay. The test proteins may be in solution or, in some cases, may be bound to a solid support.

In some embodiments, the chondroitin sulfate is selected from the group consisting of chondroitin sulfate A (CS-A), chondroitin sulfate C (CS-C), and chondroitin sulfate E (CS-E). The chondroitin sulfate may be, for example, a disaccharide or a polysaccharide.

Methods for identifying chondroitin sulfate binding protein modulators are disclosed in accordance with other embodiments of the present invention. In some embodiments, one or more chondroitin sulfate molecules are contacted with a chondroitin sulfate binding protein in the presence of one or more test compounds. The chondroitin sulfate binding protein is known to bind to a particular chondroitin sulfate in the absence of any test compounds. Test compounds that modulate binding of the target protein to the chondroitin sulfate are identified.

In some embodiments, the chondroitin sulfate is bound to a solid support, such as the surface of a cell, a glass slide, a bead or a microtiter plate. A chondroitin sulfate array may utilized. In some embodiments, a chondroitin sulfate array comprises chondroitin sulfate molecules displaying different sulfation sequences. In some embodiments, the chondroitin sulfate array comprises at least one chondroitin sulfate selected from the group consisting of chondroitin sulfate A (CS-A), chondroitin sulfate C (CS-C) and chondroitin sulfate E (CS-E).

In some embodiments, the chondroitin sulfate is selected from the group consisting of a chondroitin sulfate A (CS-A) tetrasaccharide, a chondroitin sulfate C (CS-C) tetrasaccharide, a chondroitin sulfate E (CS-E) tetrasaccharide, a CS-A disaccharide, a CS-C disaccharide and a CS-E disaccharide.

In some embodiments, a modulator is identified that is an agonist that enhances binding of the target protein to the chondroitin sulfate or to proteins with which the target protein interacts. In other embodiments, a modulator is identified that is an antagonist of the chondroitin sulfate binding protein and interferes with or diminishes binding of the target protein to the chondroitin sulfate or to proteins with which the target protein interacts.

The chondroitin sulfate binding protein may be any protein known to bind to a CS. The chondroitin sulfate binding protein may be identified using the assays described herein. In some embodiments, the target protein is selected from the group consisting of TNF-α, midkine, BDNF, NGF, FGF-16, Nogo-A, PTN, GDNF, Adam10, FGF-2, FGF-17 and ephrin A1.

In some embodiments, the test compound is a compound selected from the group consisting of: a small molecule, a protein, a peptide, and a carbohydrate.

A method of blocking binding of a chondroitin sulfate binding protein to a chondroitin sulfate is disclosed in accordance with other embodiments of the present invention. In some embodiments, the method comprises administering an antagonist of a chondroitin sulfate binding protein. Such methods can be used therapeutically. For example, administering an antagonist of TNFα binding to its cognate receptor can be used to treat inflammatory diseases in which TNFα is known to be involved. An example of such an antagonist is CS-E and analogs thereof.

Figure 1:
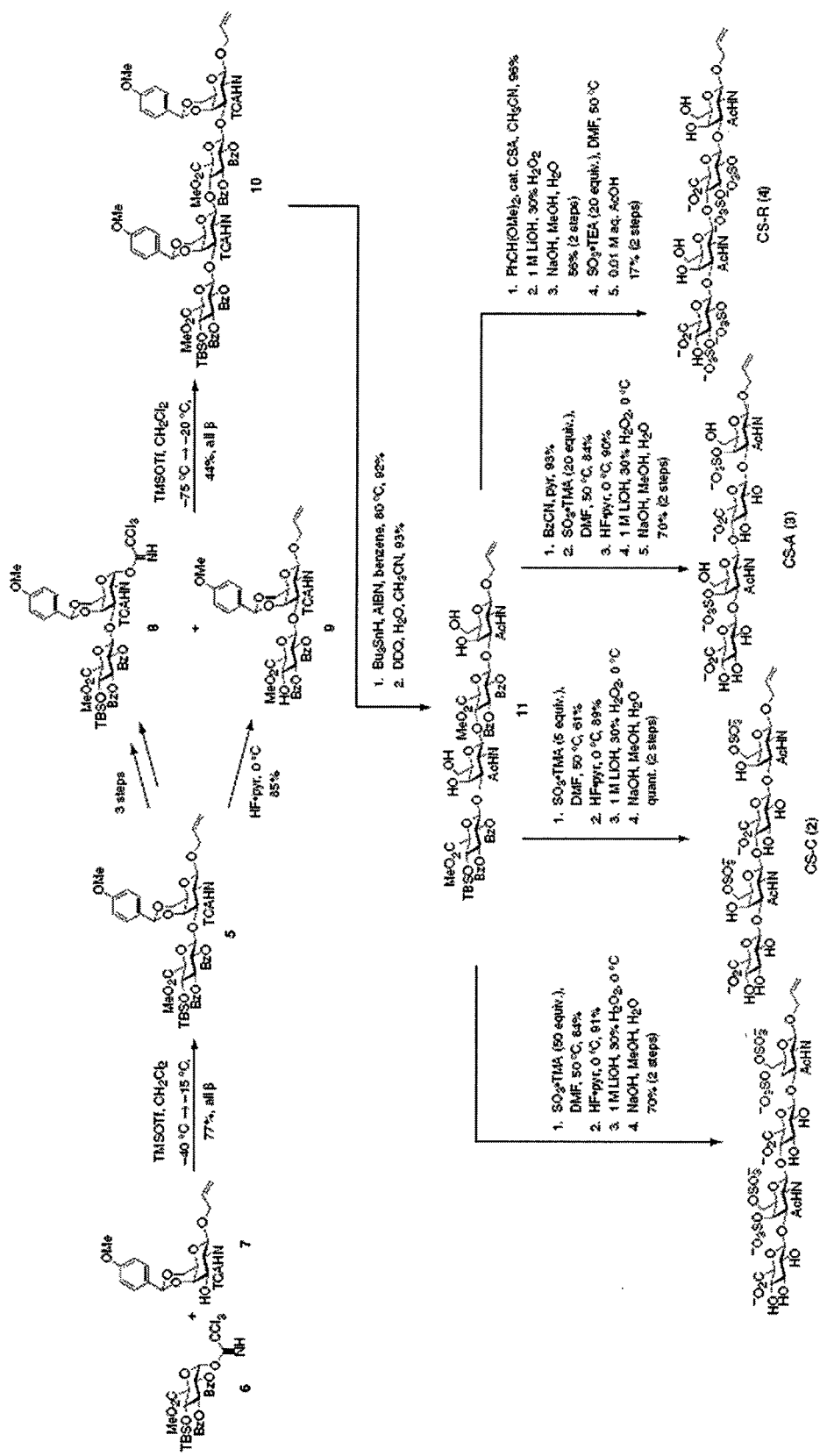
FIGS. 1A-1E depict the synthesis of CS tetrasaccharides of defined sulfation pattern, stereochemistry and chain length. Tetrasaccharides were assembled from a core disaccharide building block 5 and elaborated to install distinct sulfation motifs. This modular, convergent approach permits access to a variety of sulfation patterns, including three important sulfation motifs found in the mammalian brain (CS-E, CS-C and CS-A) and the CS-R motif, which has the same overall electrostatic charge as CS-E and can be used to evaluate further the importance of sulfate group orientation. Conversion of intermediate 11 (FIG. 1C) to CS-E (FIG. 1D), CS-C (FIG.
Figure 1A:
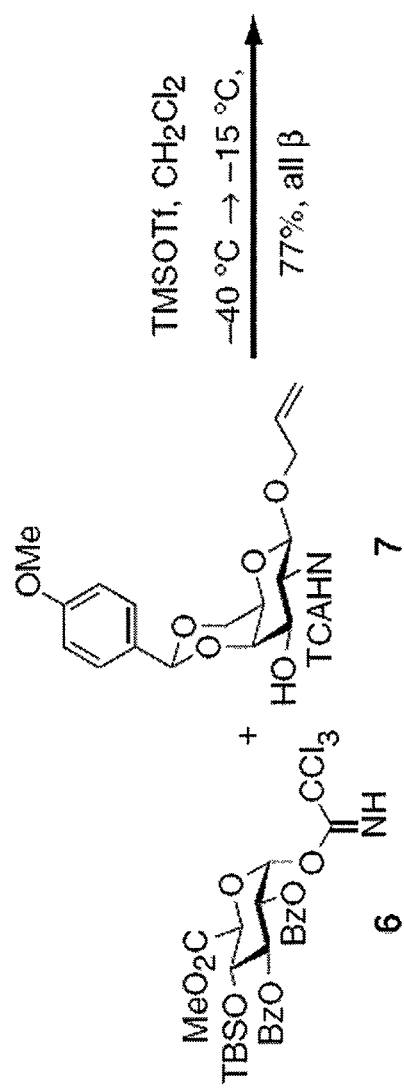
Figure 1B:
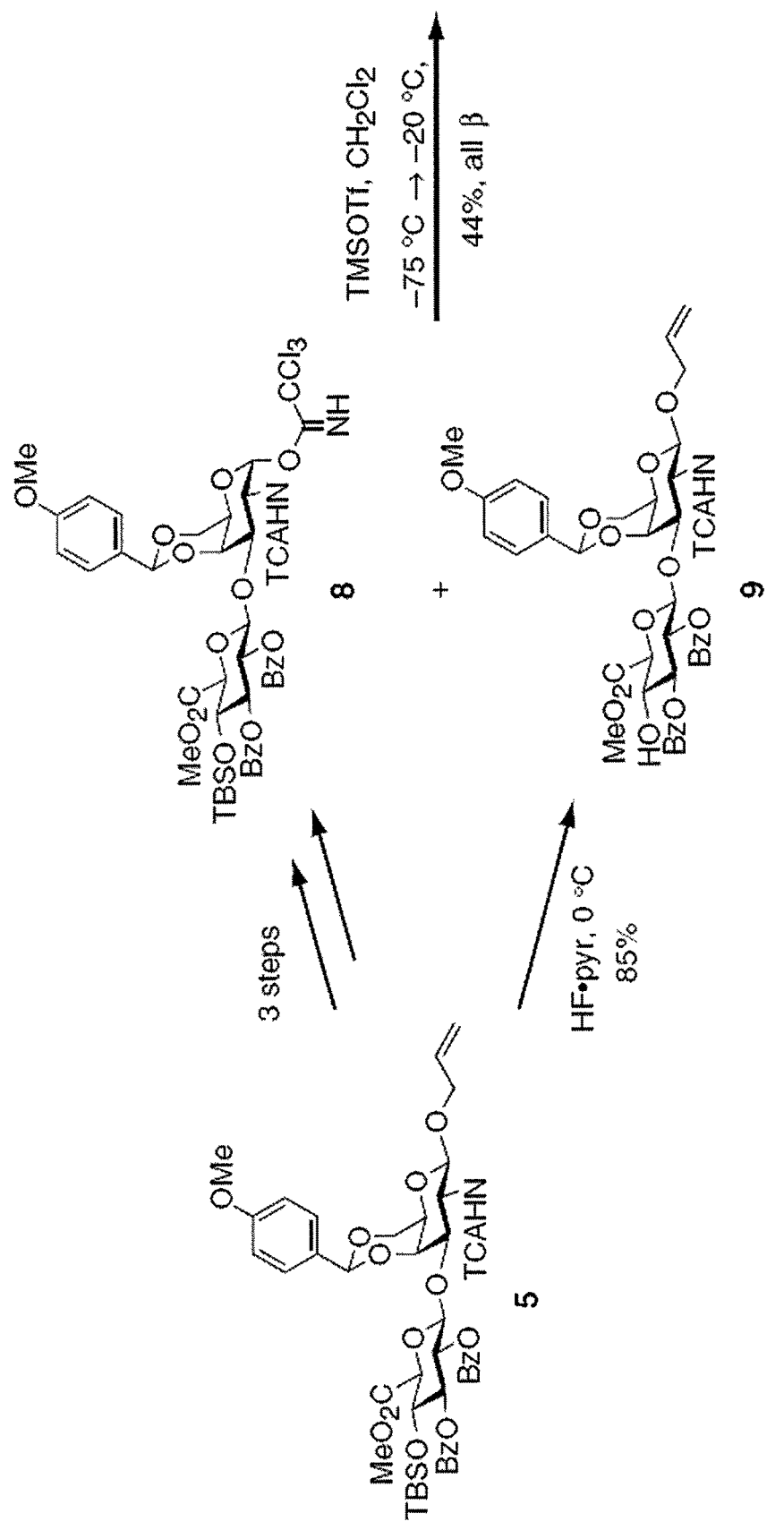
Figure 1C:
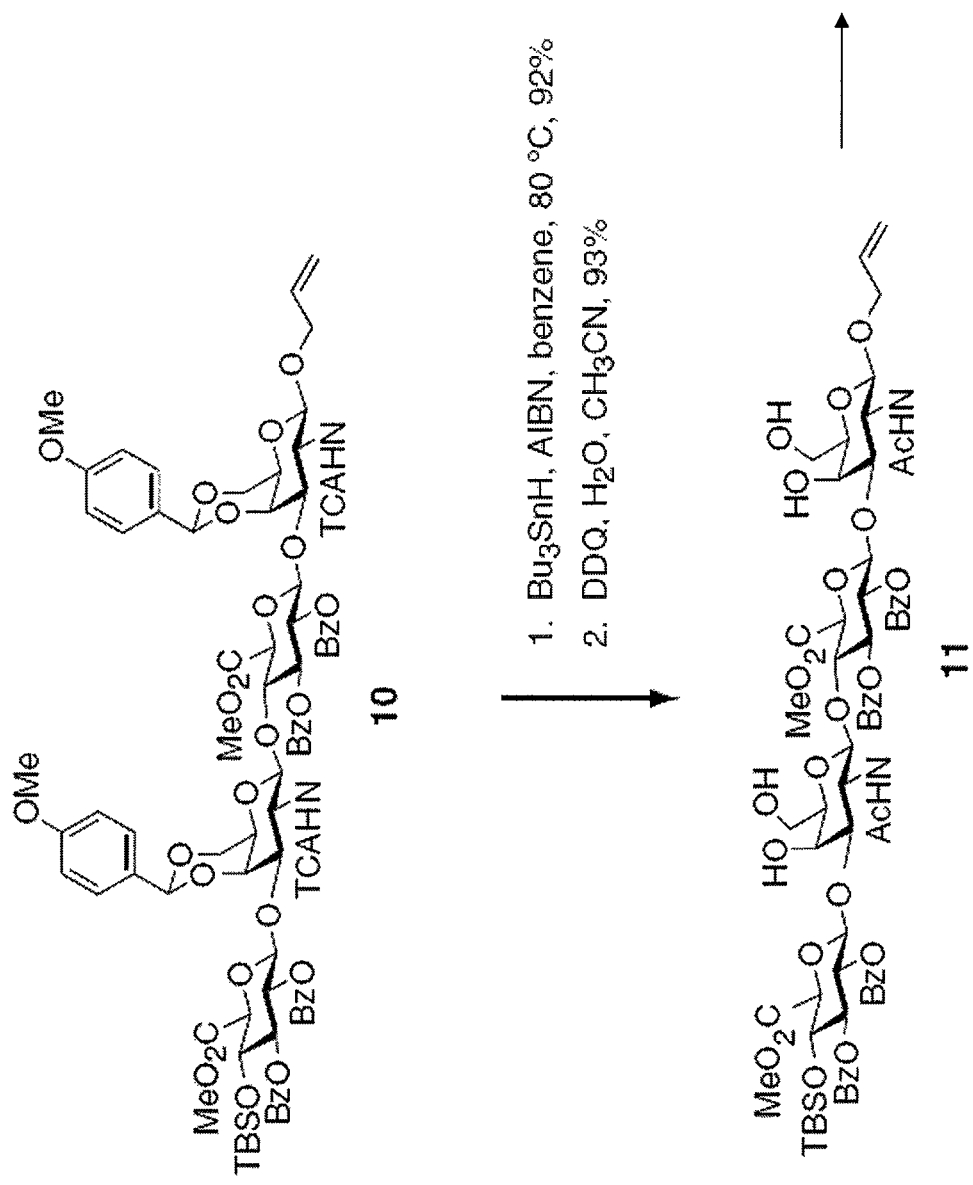

1D), CS-A (FIG. 1E) or CS-R (FIG. 1E) is achieved under the indicated conditions, respectively. The following abbreviations are used in FIGS. 1A-1E: TMSOTf, trimethylsilyl trifluoromethansulfonate; $CH_2Cl_2$, dichloromethane; HF.pyr, hydrogen fluoride-pyridine complex; $Bu_3SnH$, tri-n-butyltin hydride; AIBN, 2,2'-azobisisobutyronitrile; DDQ, 2,3-dichloro-5,6-dicyano-1,4-benzoquinone; $H_2O$, water; $CH_3CN$, acetonitrile; $SO_3$.TMA, sulfur trioxide-trimethylamine complex; DMF, dimethylformamide; LiOH, lithium hydroxide; $H_2O_2$, hydrogen peroxide; NaOH, sodium hydroxide; MeOH, methanol; BzCN, benzoyl cyanide; pyr, pyridine; $PhCH(OMe)_2$, benzaldehyde dimethyl acetal; CSA, DL-10-camphorsulfonic acid; $SO_3$.TEA, sulfur trioxide-triethylamine complex; AcOH, acetic acid; TBS, t-butyldimethylsilyl; Bz, benzoyl; TCA, trichloroacetyl; Me, methyl; Ac, acetyl.

DETAILED DESCRIPTION

Although several strategies have been suggested, no methods to systematically explore the role of specific sulfation sequences of chondroitin sulfate molecules existed prior to the developments described herein. For instance, genetic approaches that target a sulfotransferase gene perturb multiple sulfation patterns throughout the polysaccharide chain and cannot be used to study the impact of a single structural motif Holt, C. E. et al., Neuron 46, 169-172 (2005). Biochemical methods afford a mixture of heterogeneously sulfated compounds of poorly defined linear sequence (Nandini, C. D. et al., *J. Biol. Chem.* 279, 50799-50809 (2004)), thereby complicating efforts to relate a biological function to a specific sulfation sequence.

Methods for the assembly of well-defined chondroitin sulfate (CS) molecules using a convergent, synthetic approach are disclosed in accordance with some embodiments of the present invention. In some embodiments, methods are provided using chemical synthesis to separately generate oligosaccharides representing three major subclasses of CS found in vivo, CS-A, CS-C, and CS-E.

CS molecules interact specifically with certain proteins. Because of the specificity of the interactions, molecules capable of capable of enhancing or interfering with the binding of CS molecules to CS binding proteins can be used to modulate the activity of the CS binding proteins. Such molecules can, for example, directly modulate an activity of the CS binding protein, or can prevent or enhance interaction of a CS binding protein with another protein, such as a cognate receptor. In some embodiments, the present teachings provide methods of identifying CS binding proteins and methods of identifying compounds that are able to modulate the binding of the CS binding proteins to CS molecules.

Synthetic CS microarrays are also disclosed in accordance with some embodiments of the present invention. In some embodiments, the CS microarrays can be used, for example, to identify molecules that can bind to and/or interact with particular CS molecules and to identify compounds that modulate that interaction.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art, as described in various general and more specific references such as those that are cited and discussed throughout the present specification. See e.g. Singleton et al., *Dictionary of Microbiology and Molecular Biology* $2^{nd}$ ed., J. Wiley & Sons (New York, N.Y. 1994); Sambrook et al. Molecular Cloning: A Laboratory Manual (2d ed., Cold Spring Harbor Laboratory Press, Cold Spring Harbor, N.Y. (1989)), which is incorporated herein by reference. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. Standard techniques are also used for chemical syntheses, chemical analyses, pharmaceutical preparation, formulation, and delivery, and treatment of patients except to the extent otherwise described herein.

As utilized in accordance with the present disclosure, the following terms, unless otherwise indicated, shall be understood to have the following meanings:

"Monosaccharide," as used herein, refers to a polyhydroxy alcohol containing either an aldehyde or a ketone group, i.e., a simple sugar. Monosaccharide includes reference to naturally occurring simple sugars as well as simple sugars which have been chemically modified. Modified monosaccharides include, but are not limited to, monosaccharides that have increased or decreased sulfation or that have modified carboxyl, amino or hydroxyl groups.

"Polysaccharide," as used herein, refers to a linear or branched polymer of two or more monosaccharides that are linked by means of glycosidic linkages. Polysaccharides may comprise two, three, four, five, six, seven, eight, nine, ten or more monosaccharides.

"Glycosaminoglycan," as used herein, includes reference to a polysaccharide composed of repeating disaccharide units. The disaccharides contain an amino sugar (i.e., glucosamine or galactosamine) and one other monosaccharide, which can be, for example, a uronic acid (i.e., glucuronic acid or iduronic acid) as in hyaluronic acid, heparin, heparan sulfate, chondroitin sulfate or dermatan sulfate, or galactose as in keratan sulfate. The glycosaminoglycan chain can be sulfated on either moiety of the repeating disaccharide.

As used herein, "chondroitin" refers generally to chondroitin, salts thereof such as chondroitin sulfate, esters thereof, and mixtures thereof. "Chondroitin sulfate" (CS), as used herein, refers generally to at least one unit in a chondroitin sulfate chain. A chondroitin sulfate chain is a sulfated glycosaminoglycan (GAG) composed of a chain of alternating sugars (N-acetylgalactosamine and glucuronic acid).

"Chondroitin sulfate binding protein" and "CS binding protein," as used herein, refer generally to a protein that binds specifically to one or more distinct chondroitin sulfates.

"Target" and "target protein" as used herein, refer generally to a protein, protein fragment, or polypeptide that is a subject of a screen and has one or more biological properties which can be measured during the screening process.

"Agonist" as used herein, refers generally to any molecule or compound that stimulates one or more of the biological properties of a target protein. These may include, but are not limited to, small organic and inorganic molecules, peptides, peptide mimetics and agonist antibodies.

"Antagonist" as used herein, refers generally to any molecule or compound that blocks, inhibits or neutralizes, either partially or fully, one or more of the biological properties mediated by a target protein. Antagonists may include, but are not limited to, small organic and inorganic molecules, peptides, peptide mimetics and neutralizing antibodies. Antagonists specifically include molecules or compounds that prevent binding.

"Biological property" is a biological or immunological activity, where biological activity refer to a biological function (either inhibitory or stimulatory) caused by a native sequence or variant polypeptide or protein, other than the ability to induce the production of an antibody against an epitope within such polypeptide or protein, where the latter property is referred to as immunological activity. Biological properties specifically include the ability to bind a CS molecule, preferably specific binding, and even more preferably specific binding with high affinity. For example, a biological activity of TNF-α is the ability to bind and/or be activated by CS-E as described in the Examples below. Other examples of biological properties include, without limitation, the ability to mediate apoptosis and the ability to mediate neurite outgrowth.

"Linker" refers to a chemical moiety in a molecule comprising a covalent bond or a chain of atoms that covalently attaches one moiety or molecule to another, e.g. a CS to a solid support.

A linker may comprise a removable protective group. A "protective group" is a material which is bound to a molecule and can be removed upon selective exposure to an activator, such as light.

The term "solid support" refers to any solid phase material upon which a CS or test compound or protein can be attached or immobilized. For example, a solid support may comprise glass, metal, silicon, or plastic. Solid support encompasses terms such as "resin", "solid phase", and "support". A solid support can be composed of organic polymers such as polystyrene, polyethylene, polypropylene, polyfluoroethylene, polyethyleneoxy, and polyacrylamide, as well as co-polymers and grafts thereof A solid support may also be inorganic, such as glass, silica, controlled-pore-glass (CPG), or reverse-phase silica. The configuration of a solid support can be in the form of beads, spheres, particles, granules, a gel, a fiber or a surface. Surfaces can be planar, substantially planar, or non-planar. Solid supports can be porous or non-porous, and may have swelling or non-swelling characteristics. A solid support can be configured in the form of a well, depression or other container, vessel, feature or location. A plurality of solid supports can be configured in an array.

"Array" or "microarray" means a predetermined spatial arrangement of molecules, such as, for example, CS molecules, present on a substrate. The molecules can be directly attached to the substrate, or can be attached to a solid support that is associated with the substrate. The molecules may all be identical, as in the case of an array that is designed to identify proteins that bind to a single type of CS, or the molecules can be different, such as in an array that is designed to detect and/or identify proteins that bind to any of a number of different types of CS. The array may comprise one or more "addressable locations," that is, physical locations that comprise a known type of molecule. In one embodiment an addressable location comprises more than one type of molecule. However, the types of molecules present at each location are known or can be determined.

An array can comprise any number of addressable locations. In addition, the density of the addressable locations on the array can be varied. For example, the density of the addressable locations on a substrate can be increased to reduce the necessary substrate size. In some embodiments, the array format is a geometrically regular shape, which may facilitate, for example, fabrication, handling, stacking, reagent and sample introduction, detection, and storage. The array can be configured in a row and column format, with regular spacing between each location. In addition, barriers can be provided between locations to prevent undesired interactions. Alternatively, the locations can be arranged in groups, randomly, or in any other pattern. In one embodiment an array comprises a plurality of addressable locations configured so that each location is spatially addressable for high-throughput handling.

In a two-dimensional array the addressable location is determined by location on the surface. However, in one embodiment the array comprises a number of particles, such as beads, in solution. Each particle comprises a specific type or types of molecule. In this case the identity of the molecule can be determined by the characteristics of the particle. For example, the particle may have an identifying characteristic, such as shape, pattern, chromophore, or fluorophore. In other embodiments, known types of particles may be physically separated, such as in wells.

"Substrate" when used herein refers to the underlying material of an array. In some embodiments the substrate is a solid support. In one embodiment the surface of the substrate is flat. In other embodiments the surface of the substrate may comprise physical features, such as wells, trenches and raised or sunken regions. The molecules that form an array can be attached directly to the substrate, or can be attached to a solid support that is itself associated with, such as attached to or contained by, the substrate.

Preparation of Chondroitin Sulfate Tetrasaccharides

Figure 1E:
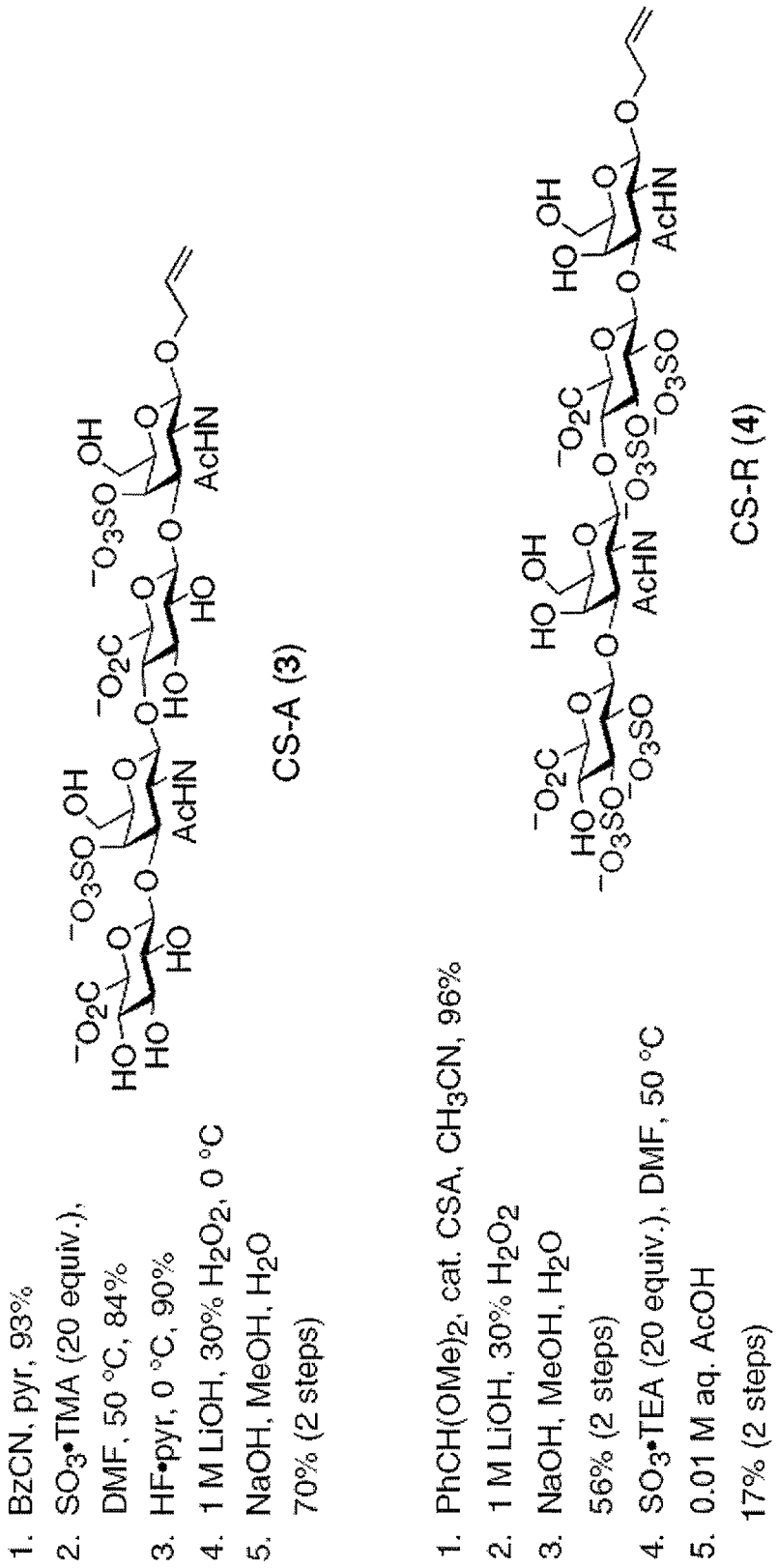

FIG. 1 show an embodiment of a chemical synthetic scheme to generate oligosaccharides representing three major subclasses of CS found in vivo CS-A, CS-C, and CS-E. Tetrasulfated molecule 1 displays the CS-E sulfation sequence, a motif enriched in the developing brain and associated with the proteoglycans appican, syndecan-1 and -4, neuroglycan C and phosphacan. Disulfated molecules 2 and 3 represent the most abundant sulfation patterns in vivo CS-C and CS-A, respectively. For comparison, tetrasulfated oligosaccharide 4, denoted CS-R, was also synthesized. CS-R possesses the same overall negative charge as 1 but has sulfate groups installed at the C-2 and C-3 positions of D-glucuronic acid (GlcA).

Details for the chemical synthesis of CS oligosaccharides are disclosed in Gama, C. I. et al., *Nat Chem Biol.* 2006 September; 2(9):467-73, which is incorporated herein by reference in its entirety. The synthetic route disclosed in FIG. 1 allows for the generation of various CS sulfation motifs from a core disaccharide building block 5. Stereocontrol in the glycosylation reactions to form β-linked oligosaccharides was achieved using α-trichloroacetimidate donors containing C-2 N-trichloroacetyl (TCA) or O-benzoyl (Bz) participating groups. An orthogonal protecting group strategy was developed to install the specific sulfation sequences. In particular, p-methoxybenzylidene and Bz groups were used to mask positions that were exposed at late stages of the synthesis for sulfation. To elongate the carbohydrate chain, a silyl ether was used to protect the C-4 position of GlcA and liberate a hydroxyl group nucleophile for reaction with a glycosylating agent. Finally, a versatile chemical handle, the allyl moiety, was appended to the reducing end of the oligosaccharides for convenient conjugation to proteins, small molecules and surfaces.

The core disaccharide building block was synthesized on a multi-gram scale from protected monosaccharides 6 and 7. For elongation of the carbohydrate chain, the disaccharide was readily converted to a suitable glycosyl donor and acceptor pair (8 and 9). Silyl deprotection of 5 using HF.pyridine followed by coupling to activated imidate 8 delivered the β-linked tetrasaccharide 10 with excellent stereoselectivity.

Radical-mediated conversion of the TCA to an N-acetyl group and oxidative cleavage of the p-methoxybenzylidene acetal afforded the key tetraol intermediate 11. Sulfation of 11 under vigorous conditions generated the precursor to CS-E and under mild conditions yielded the precursor to CS-C. The target CS-E and CS-C tetrasaccharides (1 and 2, respectively) were obtained after silyl deprotection and saponification. Synthesis of the CS-A tetrasaccharide 3 was achieved by selective benzoylation of the C-6 hydroxyl groups using benzoyl cyanide, followed by sulfation at the C-4 position. The remaining silyl and ester protecting groups were removed to afford 3. Finally, tetrasulfated 4 was generated through formation of the benzylidene acetal, which proved more stable than the p-methoxybenzylidene acetal during the sulfation reaction. Following saponification, the resulting free hydroxyl groups were sulfated and the desired CS-R tetrasaccharide obtained after deprotection of the remaining protecting groups under mildly acidic conditions. Tetrasaccharides 1-4 were purified by size-exclusion chromatography and their structures confirmed by $^1$H-NMR, proton decoupling experiments, and electrospray ionization mass spectrometry (ESI).

Identification of Chondroitin Sulfate Binding Proteins

Proteins and other molecules that interact with one or more specific chondroitin sulfates can be identified. While the methods disclosed herein generally are used to identify CS binding proteins based on their ability to bind to one specific type of CS polysaccharide, the proteins may, nonetheless, be able to bind to other types of CS or combinations of CS molecules. The test protein can be any protein, protein fragment, or polypeptide. Test proteins can be, for example, growth factors, cytokines, lectins, receptors and antibodies. In some embodiments, the test protein is a growth factor. In other embodiments, compounds other than polypeptides are tested for their ability to binds CS. In some embodiments the nature and/or identity of the test protein is known. In other embodiments, a preparation comprising multiple compounds is tested and compounds that are able to bind CS polysaccharides are identified.

In some embodiments, the methods involve providing a specific CS and contacting it with one or more test proteins. The CS molecule may be bound to a substrate or in solution. Preferably a homogeneous population of a particular CS polysaccharide with a defined sulfation pattern is used. After contacting the CS molecules with a solution comprising the test protein or proteins, binding of one or more test proteins to the CS is evaluated using methods known in the art. In some embodiments, the binding of a test protein to a CS molecule is detected by fluorescence, luminescence, Western blotting, surface plasmon resonance or other means known in the art. In one embodiment, an antibody to the test protein is utilized. The antibody, or a secondary antibody, may be conjugated with a fluorophore, such as Cy3, to facilitate detection. If the test protein binds the CS molecule, the test compound is considered a CS binding protein. A particular example of a method of screening for a protein that interacts with a CS molecule is provided in the Examples below.

The particular CS molecules used in the assays are well-defined and preferably obtained via the synthesis described above. CS molecules that may be used according to the methods provided in the embodiments described herein comprise a CS oligosaccharide. These include, for example and without limitation, CS-A disaccharides, CS-A tetrasaccahrides, CS-A octasaccharides, CS-C disaccharides, CS-C tetrasaccahrides, CS-C octasaccharides, CS-E disaccharides, CS-E tetrasaccahrides, CS-E octasaccharides, etc., or combinations thereof. In some embodiments, the CS molecule can comprise a polysaccharide enriched in a particular CS sulfation motif, such as, for example, a CS-A motif, a CS-C motif, or a CS-E motif, or combinations thereof. In some embodiments, the CS can comprise a CS oligosaccharide, a polysaccharide enriched in a particular CS sulfation motif, or combinations thereof.

In some embodiments, one or more CS molecules are attached to a surface such as a bead, a column, an array, a glass slide, a microtiter plate, the surface of a cell or a resin. The nature of the CS molecules is preferably predetermined. That is, the sulfation pattern is known. In some embodiments, one or more types of CS molecules can be present on an array. In some embodiments, the microarray is a CS microarray prepared as described herein. In some embodiments, CS molecules are non-covalently attached to poly-L-lysine (PLL)-coated glass substrates, such as slides or beads.

In some embodiments, a synthetic CS microarray can be used to identify CS binding proteins. Particular locations on the array are preferably homogeneous for a particular CS oligosaccharide and can be physically separated. In one embodiment, the CS microarray can be outlined with a hydrophobic pen to create a boundary for the protein treatments. One or more putative CS binding proteins can be contacted with the CS microarray, and incubated under conditions that allow binding. The CS microarray can then be washed to remove unbound protein and contacted with a reagent, such as, for example, an appropriate primary antibody, to detect the protein or proteins that bound to the CS on the array. Various detection strategies can be used depending on the nature of the reagent or reagents used to identify the putative CS binding protein. In the case of fluorescently labeled reagents, microarrays can be analyzed for the presence of the CS binding protein using methods well known in the art, for example, a GenePix 5000a scanner.

The use of distinct labels can allow for the detection of multiple CS binding proteins simultaneously or in sequence using the same microarray. Thus, in some embodiments the CS is contacted with two or more putative CS binding proteins.

In other embodiments, test proteins can be provided on a solid support and contacted with CS in solution. After a period of time sufficient to allow binding, unbound CS is removed, for example by washing. Binding of CS to an immobilized test protein can be determined using, for example, an antibody to the CS. In some embodiments a single type of test protein may be immobilized and contacted simultaneously or sequentially with various CS polysaccharides. In other embodiments multiple test proteins are present, for example in known locations on an array and assayed together. The use of multiple antibodies with different labels can allow for the simultaneous identification of each type of CS that is able to bind to the immobilized test proteins.

In some embodiments the CS molecule may be present in a solution when it is contacted with one or more test proteins, rather than being affixed to a substrate. CS binding proteins can be identified, for example, by immunoprecipitating the CS molecule along with any CS binding proteins, using an antibody to the putative binding protein. If a putative binding protein is unknown, it could be immunoprecipitated using an anti-CS antibody and identified.

In some embodiments, the CS molecule can be contacted with a solution comprising a mix of proteins prepared from cells. Such preparations may be from cells associated with an area in which chondroitin sulfates are believed to play a role in a cellular process. For example, the CS molecule can be contacted with a solution prepared from a neural cell lysate. In some embodiments, such as this, the nature of the putative CS binding proteins is not known, but can be determined by isolating the protein based on its ability to bind to CS, either in solution or attached to a substrate.

After the CS molecule is contacted with one or more test proteins, the CS molecule, along with any test proteins that are bound to it, can be isolated using, for example, an anti-CS antibody (or an antibody to the binding protein if it is known). Antibodies useful for isolating the CS molecule can be, for example, any antibody which recognizes the particular CS molecule used in the assay. In some embodiments, the antibodies can be attached to a surface, such as, for example, a bead, a column, an array, a glass slide, a microtiter plate, or a resin.

Although the particular methods described above refer to the identification of CS binding proteins, one of skill in the art would understand that such methods can be readily applied to identify other types of molecules that bind CS, such as small molecules, peptides, aptamers and the like.

Identification of Modulators of Chondroitin Sulfate Binding Proteins

Modulators of proteins that interact with a CS binding protein can be identified in accordance with some embodiments of the present invention. The CS binding protein may be identified by the methods disclosed herein or may be otherwise known to interact with one or more CS molecules. A modulator can be any small molecule, protein, peptide, carbohydrate, polymer, etc. including, for example, CS polysaccharides, analogs of chondroitin sulfate, and oligomers and polymers of such small molecules. In some embodiments, modulators are synthetic polymers that display CS oligosaccharides. In some embodiments, modulators of CS binding proteins can include the molecules described in U.S. patent application Ser. No. 11/140,618 ("the '618 application") published as U.S. Patent Application Publication No. 2006/0025379, which is incorporated herein by reference in its entirety. In some embodiments, a modulator can be successively modified through traditional medicinal chemistry, combinatorial chemistry and structure-based design approaches. Such modification can be used to, for example, develop more selective or more potent modulators.

A modulator of a CS binding protein can act, for example, either as an agonist or an antagonist. In some embodiments, the modulator is an antagonist of a CS binding protein and can reduce or block binding of a CS binding protein to a CS molecule. In some embodiments, the modulator is an agonist of a CS binding protein and can enhance binding of the CS binding protein to a CS molecule. Binding of the CS protein to other proteins can be mediated by or influenced by CS. Thus, a modulator of a CS binding protein may also be able to modulate the interactions of the CS binding protein with a protein to which it binds. An agonist could enhance such binding, while an antagonist could reduce or inhibit such binding. For example, as described herein CS-E or an analog thereof can be used as an antagonist to inhibit the interaction of TNFα and TNFR.

In some embodiments, methods of screening for a modulator that interacts with a target CS binding protein are provided. Competition binding assays and direct binding assays can be used.

In some embodiments a competition assay is used to screen for a modulator that interacts with a target CS binding protein to either enhance or inhibit its ability to bind to a CS. The competition assay can, for example, involve providing a CS molecule, which is contacted with a target CS binding protein in the presence of one or more test compounds. Binding of the target CS binding protein to the CS molecule is then assessed. If the binding of the CS binding protein to the CS molecule is modulated in the presence of a test compound, the test compound is identified as a modulator of the target CS binding protein. If the binding of the CS binding protein to the CS molecule is blocked or reduced in the presence of a test compound, the test compound is an inhibitor or antagonist of CS binding. On the other hand, if binding of the CS binding protein in the presence of the test compound is enhanced, the test compound can be considered an agonist of CS binding.

Binding can be determined using an appropriate assay as can be determined by the skilled artisan. In some embodiments, binding of the target CS binding protein to the CS molecule can be determined using an immunoassay, as known to those skilled in the art. In other embodiments, direct binding of the target protein to a particular modulator on a surface can be determined by surface plasmon resonance.

CS molecules suitable for use according to the methods provided are essentially as described above with respect to the methods of identifying a CS binding molecule. In fact, the assays described above for identifying CS binding molecules can be modified by the addition of a test compound to determine the ability of the test compound to interfere with CS binding.

In some embodiments, after the CS molecule is contacted with the CS binding protein in the presence of one or more test compound, the CS molecule, along with any target CS binding proteins or test compounds that can be binding to it, can be isolated using, for example, an anti-CS antibody or an antibody to the CS binding protein. Antibodies useful for isolating the CS molecule can be any antibody which recognizes the CS molecule. In some embodiments, the antibodies can be attached to a surface, such as, for example, a bead, a column, an array, a glass slide, a microtiter plate, or a resin. In this way, a particular test compound that binds to one or both of the CS binding protein and the CS molecule can be isolated and, if necessary, identified.

In some embodiments, multiple test compounds are screened simultaneously. For example a pool of test compounds can be screened for its ability to modulate binding of a CS binding protein to a CS. If activity is observed, the pool can be divided and subdivided to determine the particular test compound responsible for the activity.

The CS binding protein can be any protein that binds specifically to one or more distinct chondroitin sulfates. In some embodiments, the target protein can be, for example, TNF-α, midkine, BDNF, NGF, FGF-16, Nogo-A, PTN, GDNF, Adam10, FGF-2, FGF-17 or ephrin A1. In some embodiments, the target protein can be a growth factor.

In some embodiments, potential modulators can be identified in a direct binding assay in which one or more test compounds are provided and contacted with a CS binding protein. In some embodiments preferred test compounds include CS molecules and variants and analogs of CS molecules. In particular, in some embodiments the ability of a CS binding protein to bind a particular CS molecule is identified as described herein. Following the identification, analogs of the particular CS molecule can be screened using the direct binding assay (or in the competition assays described above) for their ability to bind to the CS binding protein.

Binding of a test compound to a CS binding protein is assessed using, for example, an immunoassay or surface plasmon resonance. If the test compound binds to the CS binding molecule, the test compound can be further tested to determine whether it can modulate a biological activity of the CS binding protein, such as the ability of the CS binding protein to bind to CS.

In some embodiments, one or more test compounds can be attached to a surface such as a glass slide or microtiter plate. The test compounds can be present in the form of an array. Binding of the CS binding protein to the immobilized test compound can be identified, for example, using an antibody to the CS binding protein, fluorescence, luminescence, Western blotting, surface Plasmon resonance, or other known methods.

Once a compound is identified as able to bind a CS binding protein and/or able to modulate the binding of the CS protein to a particular CS polysaccharide, the test compound can be tested for its ability to modulate an additional activity of the CS binding protein. For example, if the CS binding protein is a ligand for a receptor, the ability of the test compound to modulate binding of the ligand to its cognate receptor can be measured. Similarly, if a biological activity of the test compound is known, such as its role in cell growth or apoptosis, the ability of the test compound to modulate this activity can be determined.

As described in the Examples below, TNF-α was identified as selectively binding to a CS-E tetrasaccharide. In one embodiment, the ability of one or more test compounds to modulate the binding of TNF-α to CS-E is tested. The CS-E may be immobilized on a substrate, such as a glass slide as described herein, or may be free in solution. Binding may be determined utilizing an anti-TNFα antibody. In this way, agonist and/or antagonists of TNFα binding to CS-E can be identified.

In another embodiment, test compounds are tested for their ability to inhibit the interaction of TNFα and its cognate receptor, essentially as described in Example 2. IN another embodiment, test compounds are tested for their ability to prevent apoptosis mediated by TNFα. The test compound may be one identified as able to modulate the binding of TNFα to CS-E in the assay described above.

Nogo-A is another known CS binding protein. The assays described above can be utilized to identify the particular CS molecules that Nogo-A binds. In one embodiment the ability of a test compound to modulate Nogo-A binding to the identified CS is determined. In another embodiment, the ability of a test compound to modulate Nogo-A dependent neurite outgrowth is measured.

Chondroitin Sulfate Microarrays

In some embodiments, arrays of synthetic CS molecules are formed on a substrate. Synthetic CS molecules can be arranged directly on a substrate for use in, for example, the identification of one or more CS binding molecules or one or more modulators of CS binding molecules. The CS molecules can be attached to the substrate via linkers, using methods well known in the art and as described herein. Alternatively, the CS molecules can be synthesized directly on the substrate. In some embodiments, CS molecules are non-covalently attached to PLL coated substrates, preferably glass slides. Antibodies to specific CS molecules can be used to determine that the array is composed of the desired CS molecules.

In a typical array a substrate comprises one or more addressable locations of CS molecules. The addressable locations can be directly adjacent to each other or can be physically separated by a gap or a barrier.

In some embodiments, each addressable location comprises one type of CS molecule, for example CS-A, CS-C or CS-E. However, in other embodiments, at least one addressable location comprises more than one type of CS molecule. In addition to the different subtypes of CS molecules, CS molecules may also differ in the length of the oligosaccharide chains. For example, disaccharides or tetrasaccharides may be used.

In the case where each location comprises a single type of CS molecule, the number of locations on the array of CS molecules is at least as great as the number of different types of CS molecules to be used. In one embodiment, each addressable location comprises at least about $10^5$ CS molecules.

In some embodiments, the CS molecule composition and physical location of each addressable location is known. In one embodiment, each of the addressable locations in the array comprises a different type of CS molecule. For example, if a target protein is to be assayed for its ability to bind CS-A, CS-C and CS-E, the array may comprise three addressable locations, each comprising a different type of CS molecule. In an alternative embodiment, more than one addressable location comprising a particular type of CS molecule is present. In some embodiments, the particular location of a particular type of CS molecule is not predetermined, but can be identified using antibodies to the CS molecules.

The overall size of the array is not limited and will be determined based on a variety of factors, including the number of CS molecules in each addressable locations, the number of addressable locations and the physical nature of the solid support on which the array is formed.

In some embodiments, a CS microarray can be created using a general, highly efficient strategy for attaching synthetic oligosaccharides to the array surface, details of which are provided in Tully, S. E. et al., *J. Am. Chme. Soc.* (2006) 128:7740-7741; Gama, C. I. et al., *Nature Chemical Biology* (2006) 2(9):467-473; and Shipp, E. L. and Hsieh-Wilson, L. C., *Chemistry & Biology* (2007) 14:195-208; each of which are incorporated herein by reference in its entirety. Briefly, CS molecules displaying different sulfation sequences are synthesized with an allyl functionality on the reducing end of the sugar. This group is stable to the chemical manipulations used to synthesize the oligosaccharides, yet it can be readily functionalized for surface conjugation. Ozonolysis of, for example, CS-A tetrasaccharide, CS-C tetrasaccharide, CS-E tetrasaccharide and CS-E disaccharide, can be followed by treatment with 1,2-(bisaminooxy)ethane to furnish CS oligosaccharides with a convenient aminooxy handle for covalent attachment to aldehyde-coated glass slides or other substrates.

In a particular embodiment, solutions of aminooxy oligosaccharides in buffer (for example, 300 mM $NaH_2PO_4$, pH 5.0) can be arrayed on slides, such as Hydrogel Aldehyde slides (NoAb Biodiscoveries) by using a robotic arrayer, such as a Microgrid 11 arrayer (Biorobotics), to deliver sub-nanoliter volumes. In one embodiment, for example, spots are approximately 1 to 1000 μm, more preferably 1 to 500 μm and in some embodiments about 100-200 μm in diameter. In some embodiments, concentrations of carbohydrates range from 0-1000 μM. The resulting arrays can be incubated in a 70% humidity chamber at room temperature overnight and then stored in a low humidity, dust-free dessicator prior to use.

Importantly, this strategy requires minimal manipulation of the sulfated oligosaccharides, enabling their direct conjugation in two short, high-yielding steps. Moreover, the approach is compatible with standard DNA robotic printing and fluorescence scanning technology, which requires only minimal amounts of material and allows a large number of molecular interactions to be probed simultaneously.

Antibodies selective for specific CS sulfation motifs can be used to test the CS microarrays. Unreacted aldehyde groups can be quenched, for example with $NaBH_4$. The microarrays can then be incubated with monoclonal antibodies raised against the particular CS molecules used in the array and binding visualized using standard techniques. In the array described in Example 2, below, antibodies were raised against CS-A tetrasaccharide or CS-E tetrasaccharide conjugated to keyhole limpet hemocyanin, and antibody binding was visualized using a secondary Cy3-conjugated goat anti-mouse antibody. The CS-A antibody bound to the CS-A tetrasaccharide in a concentration-dependent manner, and strong selectivity for the CS-A motif was observed, with little detectable binding to the CS-C or CS-E sulfation motifs. Similarly, the CS-E antibody selectively recognized the CS-E tetrasaccharide and displayed only weak binding to the CS-C motif at high tetrasaccharide concentrations.

In some embodiments for identifying a CS binding protein, one or more known test proteins are contacted with an array of CS molecules. Binding of the test protein to the array is detected using, for example an antibody to the test protein. A test protein that binds to the CS array is identified as being a CS binding protein. In other embodiments, the array is contacted with one or more unknown proteins and proteins that bind to the array are identified using known methods. Once the ability of a particular protein to bind to a CS array is determined, the array can be used to determine whether one or more test compound modulate the binding.

In one embodiment an array is prepared comprising CS-A, CS-C and CS-E in three different addressable locations and contacted with one or more known proteins. Binding of the protein, if any, to CS molecules at one or more of the addressable locations is determined, for example by using an antibody to the known protein. The arrays can also be used to identify compounds that modulate the ability of any identified protein to bind to CS molecules.

Uses of Modulators of Chondroitin Sulfate Binding Proteins

Modulators of CS binding proteins can be used for a variety of purposes, including, for example, for inhibiting or enhancing a biological property of a CS binding protein. In some embodiments, the modulator can be used to block interaction of CS binding proteins to other proteins, or to block another biological property of a CS binding protein. In some embodiments, the modulator can be used in solution to block binding of a CS binding protein to another protein.

Biological properties of CS binding proteins can include a wide variety of activities and functions. For example, such biological properties can include binding to another protein, the ability to mediate apoptosis, the ability to mediate neurite outgrowth, the ability to mediate cell proliferation, the ability to mediate cell growth, the ability to mediate neuronal regeneration, the ability to mediate/block the entry of microorganisms (e.g., malaria, viruses, bacteria), the ability to modulate immune and inflammatory responses and the ability to mediate cell migration.

Modulators of the ability of CS binding proteins to bind CS can be tested for their ability to act as an agonist or antagonist of another biological property of the CS binding protein. For example, in cases where a CS binding protein is known to bind to a receptor, the modulator can be tested for its ability to agonize or antagonize the interaction of the CS binding protein with its cognate receptor. For example, as described in detail in the Examples section below, CS-E was shown to specifically bind to TNF-α and modulate the interaction of TNF-α with the TNF receptor (TNFR1). Cognate receptors are known for a number of the CS binding proteins. For example, Nogo-A binds to NgR (Fournier, A. E. et al., *Nature* 409,341-346 (2001)); BDNF binds to trkB (Marsh et al. *Journal of Neuroscience*, Vol 13, 4281-4292 (1993)).

In cases were a CS binding protein is known to mediate a biological activity, such as, for example, apoptosis, the modulator can be tested for its ability to agonize or antagonize apoptosis. In some embodiments, cell based assays can be used that can be dependent on the CS binding protein. For example, when the CS binding protein is TNF-α, the modulator can be tested for the ability to prevent apoptosis. As another example, when the CS binding protein is Nogo-A, a cell-based assay for neurite outgrowth can be used.

CS-E was shown to antagonize the interaction of TNFα with TNFR1. Thus, in some embodiments, CS-E or a polysaccharide enriched in CS-E is used to reduce or prevent TNFα binding to TNFR1. TNFα is known to be a primary cytokine involved in a number of diseases including rheumatoid arthritis, Crohn's disease and psoriasis. Thus, in other embodiments CS-E tetrasaccharide or another polysaccharide enriched in CS-E is used to treat a patient suffering from a disease associated with TNFα activity, such as rheumatoid arthritis, Crohn's disease and psoriasis. The CS-E is preferably administered to a patient suffering from the disease or disorder in conjunction with a physiologically acceptable carrier. The mode of administration and the dosing regimen will be as determined by the skilled practitioner.

EXAMPLES

The following examples are offered by way of illustration and not by way of limitation.

Example 1

This example illustrates the identification of novel CS-binding proteins using a CS microarray. This example illustrates the identification of tumor necrosis factor-α (TNF-α) to chondroitin sulfate-E (CS-E)).

The CS microarrays in this example were prepared as describe above. Prior to use, the arrays were outlined with a hydrophobic pen (Super Pap Pen, Research Products International) to create a boundary for the protein treatments and rinsed three times with $H_2O$. The slides were then blocked by treatment with $NaBH_4$ (125 mg) in 140 mM NaCl, 2.7 mM KCl, 5.4 mM $Na_2HPO_4$, and 1.8 mM $KH_2PO_4$ (phosphate buffered saline, PBS, 50 mL) at room temperature (rt) for 5 min and washed five times for 3 min with PBS. Human TNF-α (Peprotech), FGF-1 (R&D Systems; both reconstituted to 2 μM 0.1% TRITON X-100 (TRITON X-100 is a commercially available version of polyethylene glycol p-(1,1,3,3-tetramethylbutyl)-phenyl ether) in PBS), cell culture supernatant containing monoclonal anti-CS-A antibody, or cell culture supernatant containing monoclonal anti-CS-E antibody (both 1:1 in 0.1% TRITON X-100 in PBS) were spotted onto the slides in 250 μL quantities, and incubated at rt for 2 h in a humidity chamber. The slides were then washed as previously described and incubated with the appropriate primary antibody (anti-TNF-α (Peprotech) or anti-FGF-1 (R&D Systems); 1:1000 in 0.1% TRITON X-100 in PBS) for 2 h at rt. Following the incubation, the slides were washed as previously described and treated in the dark at rt with a secondary IgG antibody conjugated to Cy3 (Amersham; 1:5000 in 0.1% TRITON X-100 in PBS) at rt for 1 h. The slides were washed three times for 2 min with PBS, two times for 1 min with $H_2O$ and dried under a gentle stream of $N_2$.

Microarrays were analyzed at 532 nm using a GenePix 5000a scanner, and fluorescence quantification was performed using GenePix 6.0 softwcan be after correction for local background. Each protein was analyzed in triplicate, and the data represent an average of at least five spots for a given carbohydrate concentration. All solutions used for the carbohydrate microarrays were sterile-filtered through a 0.2 μm syringe filter prior to use.

Selective binding of TNF-α to the CS-E tetrasaccharide was observed on the microarray, with little or no binding to the CS-A or CS-C motifs. As a negative control, fibroblast growth factor-1 (FGF-1), which does not interact with CS, displayed no appreciable binding to the carbohydrate microarray.

Example 2

This example illustrates the ability of polysaccharides enriched in the CS-E sulfation motif to antagonize the TNF-α interaction with the cell surface receptor TNFR1.

TNFR1 was immobilized on a microtiter plate, and binding of TNF-α to the receptor was measured in the presence of varying concentrations of the CS-E tetrasaccharide or naturally occurring CS polysaccharides. Human recombinant TNFR1 (Peprotech; 1 μg/mL in 50 mM $Na_2CO_3$, pH 9.6) was added to a 384-well NUNC Maxisorp clear plate (25 μL per well), and the plate was sealed and incubated for 12 h at 4° C. The wells were aspirated, washed four times with PBS containing 0.05% TWEEN-20 (TWEEN-20 is a commercially available version of Polysorbate 20) (PBST, 75 μL/wash), and blocked for 2 h at rt with 1% BSA in PBS (75 μL). During this time, biotinylated TNF-α (Perkin Elmer; 25 μL/well of a 1 nM solution in 0.05% TWEEN-20, 0.1% BSA in PBS) was pre-incubated with the indicated concentrations of polysaccharides enriched in the CS-A, CS-C; or CS-E motifs (Seikagaku; 0.1-100 μM in $H_2O$) or CS-E tetrasaccharide (0.01-5 mM in $H_2O$). After the blocking step, the plate was washed four times with PBST, and the solutions of CS and TNF-α were added to the wells and incubated at rt for 2 h. Following aspiration, the wells were washed four times with PBST and treated with streptavidin-HRP (Pierce; 25 μL/well, 1:2000 in 0.05% TWEEN-20, 0.1% BSA in PBS) for 30 min at rt. The wells were again aspirated, washed four times with PBST, and then developed with ABTS liquid substrate solution (Sigma; 25 μL/well, solution at rt) for 30 min at rt. Color development was monitored on a Victor plate reader (PerkinElmer) at 405 nm. Each carbohydrate concentration was analyzed in triplicate, and the absorbance values were corrected for background in the absence of carbohydrate and normalized with respect to the absorbance value at the lowest carbohydrate concentration.

Both CS-E tetrasaccharide and polysaccharides enriched in the CS-E sulfation motif inhibited the interaction between TNF-α and TNFR1. In contrast, polysaccharides enriched in the CS-C or CS-A motifs could not antagonize the TNF-TNFR1 interaction. Potency measurements showed a median inhibitory concentration (relative $IC_{50}$) for the CS-E polysaccharide of 13.7±2.5 μM. Although the potency of the tetrasaccharide (relative $IC_{50}$ of 343.9±37.8 μM) was reduced relative to the polysaccharide, the activity of the two compounds is comparable (25-fold difference) given that the polysaccharide is estimated to contain 37 CS-E tetrasaccharide epitopes. Notably, the $IC_{50}$ values can be within the physiological concentration range of CS, which is estimated to be at least 60 μM in the brain and may exist at 5- to 10-fold higher local concentrations at the cell surface and in the extracellular matrix.

Example 3

This example illustrates the ability of polysaccharides enriched in the CS-E sulfation motif to inhibit TNF-α-induced cell death.

U937 cells (A TCC) sensitive to TNF-α-induced apoptosis were cultured in RPMI 1640 medium containing 10% fetal bovine serum at 37° C. and 5% $CO_2/0_2$. Cells were grown in every other well of a 384-well NUNC sterile, clear plate (25,000 cells/well, 25 μL/well) for 18 h. Solutions of the CS-E tetrasaccharides and CS polysaccharides enriched in the CS-E sulfation motif at various concentrations (0.01-4000 μM in sterile PBS) were pre-incubated with TNF-α (1 μL/well of a 125 ng/mL solution in sterile PBS) at rt. After 2 h, the solutions were added to the cells and incubated for 18 h. At this time, caspase 3/7 activity was analyzed using the Apo-One homogeneous caspase 3/7 assay kit (Promega) according to the manufacturer's protocol. Readings were taken every 30 min for 18 h at rt on a Victor plate reader. By this time, caspase 3/7 activity had reached a plateau, and the endpoints of the various treatments were used for data analysis. Endpoint fluorescence values for controls containing only cells were subtracted from the experimental endpoint values, and the resulting values were then normalized with respect to that of the lowest carbohydrate concentration. Each carbohydrate concentration was repeated in triplicate.

The extent of apoptosis was determined by monitoring the production of caspases 3 and 7 using a fluorescent rhodamine-DEVD peptide substrate. Both CS-E tetrasaccharide and CS polysaccharides enriched in the CS-E sulfation motif prevented the cells from undergoing apoptosis, effectively blocking cell death (FIG. 4). Interestingly, treatment of the cells with high concentrations of either compound reduced the extent of cell death compared to cells not treated with TNF-α, suggesting that the compounds may exert a protective function. The CS-E tetrasaccharide and polysaccharide had no effect on the extent of apoptosis in the absence of TNF-α.

All numbers expressing quantities of ingredients, reaction conditions, and so forth used in the specification and claims can be to be understood as being modified in all instances by the term "about." Accordingly, unless indicated to the contrary, the numerical parameters set forth in the specification and attached claims can be approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The invention illustratively described herein suitably can be practiced in the absence of any element or elements, limitation or limitations that is not specifically disclosed herein. The terms and expressions which have been employed can be used as terms of description and not of limitation, and there is no intention that in the use of such terms and expressions indicates the exclusion of equivalents of the features shown and described or portions thereof. It is recognized that various modifications can be possible within the scope of the invention disclosed. Thus, it should be understood that although the present invention has been specifically disclosed by preferred embodiments and optional features, modification and variation of the concepts herein disclosed can be resorted to by those skilled in the art, and that such modifications and variations can be considered to be within the scope of this invention as defined by the disclosure.

All patents and publications are herein incorporated by reference in their entireties to the same extent as if each individual publication was specifically and individually indicated to be incorporated by reference.

What is claimed is:

1. A composition comprising homogeneous populations of chondroitin sulfate carbohydrates, wherein each homogeneous population of chondroitin sulfate carbohydrates is immobilized on an addressable location on a substrate, wherein each of said addressable locations is homogeneous for a particular chondroitin sulfate carbohydrate, wherein each of said addressable locations is separate from another addressable location, wherein said substrate comprises two or more addressable locations comprising chondroitin sulfate carbohydrates displaying different sulfation sequences, and wherein said chondroitin sulfate carbohydrates are selected from the group consisting of chondroitin sulfate A, chondroitin sulfate C, and chondroitin sulfate E.

2. The composition of claim 1, wherein the substrate comprises a bead or a particle.

3. The composition of claim 2, wherein the bead or particle comprises a paramagnetic bead or particle.

4. The composition of claim 2, wherein the bead or particle comprises one or more of agarose, polystyrene, cellulose, cellulose acetate, carboxymethylcellulose, alginate, polyacrylamide, polyacrylate, polymethacrylic acid, polyvinylchloride, polytetrafluoroethylene, polyvinylacetate, silica, or glass.

5. The composition of claim 1, wherein the substrate comprises a glass substrate.

6. A composition comprising one or more homogeneous populations of chondroitin sulfate carbohydrates, wherein each of the one or more homogeneous populations of chondroitin sulfate carbohydrates is immobilized on an addressable location on a substrate, wherein each of said addressable locations is homogeneous for a particular chondroitin sulfate carbohydrate, wherein said each of said addressable locations is separate from another addressable location of chondroitin sulfate carbohydrate on the substrate, and wherein the substrate comprises a poly-Lysine coated substrate.

7. The composition of claim 6, wherein the poly-Lysine comprises poly-D-Lysine.

8. The composition of claim 6, wherein the poly-Lysine comprises poly-L-Lysine.

9. The composition of claim 6, wherein the CS molecules are non-covalently attached to a glass substrate.

10. The composition of claim 6, wherein the CS molecules are covalently attached to the glass substrate.

11. The composition of claim 1, wherein the CS is attached to the solid support in the form of an array.

12. The composition of claim 11, wherein the chondroitin sulfate is selected from the group consisting of: a chondroitin sulfate A (CS-A) tetrasaccharide, a chondroitin sulfate C(CS-C) tetrasaccharide, a chondroitin sulfate E (CS-E) tetrasaccharide, a CS-A disaccharide, a CS-C disaccharide and a CS-E disaccharide.

13. The composition of claim 1, wherein each population of chondroitin sulfate comprises a chondroitin sulfate selected from the group consisting of: a chondroitin sulfate A (CS-A) tetrasaccharide, a chondroitin sulfate C(CS-C) tetrasaccharide, a chondroitin sulfate E (CS-E) tetrasaccharide, a CS-A disaccharide, a CS-C disaccharide and a CS-E disaccharide.

14. The composition of claim 1, wherein the CS polysaccharides are tetrasaccharides.

15. The composition of claim 1, wherein the CS polysaccharides are disaccharides.

16. The composition of claim 1, wherein said substrate is a poly-L-lysine coated glass substrate.

* * * * *

UNITED STATES PATENT AND TRADEMARK OFFICE
CERTIFICATE OF CORRECTION

PATENT NO.         : 8,623,610 B2
APPLICATION NO.    : 11/751880
DATED              : January 7, 2014
INVENTOR(S)        : Gama et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this
Nineteenth Day of May, 2015

Michelle K. Lee
*Director of the United States Patent and Trademark Office*